US00PP37503P2

(12) United States Plant Patent
Mathey

(10) Patent No.: US PP37,503 P2
(45) Date of Patent: Jun. 30, 2026

(54) ***SPIRAEA* PLANT NAMED 'SMNSBDOU'**

(50) Latin Name: *Spiraea betulifolia*
Varietal Denomination: SMNSBDOU

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,945

(22) Filed: Oct. 28, 2025

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP26,995 P3 * 8/2016 Wood ..... Plt./226

* cited by examiner

*Primary Examiner* — Karen M Redden

(57) ABSTRACT

A new and distinct cultivar of *Spiraea* plant named 'SMNSBDOU' is disclosed, characterized by abundant, fragrant, bright pink flowers on plants with a tidy, rounded habit Foliage is chartreuse when mature, with an orange tint. Fall foliage is vibrant orange and burgundy. Plants have shown excellent performance both in containers and in the landscape. The new cultivar is a *Spiraea*, typically produced as an outdoor ornamental plant.

5 Drawing Sheets

Latin name of the genus and species: *Spiraea betulifolia*.
Cultivar denomination: 'SMNSBDOU'.

BACKGROUND OF THE INVENTION

The new cultivar is a product of a planned breeding program conducted by the inventor to produce new *Spiraea* foliage colors, flower colors, and forms. The seed parent is an unnamed *Spiraea betulifolia* selection. The pollen parent is unknown. The open pollination resulting in the new cultivar was made in summer 2017 at a nursery in Grand Haven, Michigan.

*Spiraea* 'SMNSBDOU' was found and selected at the same nursery in Grand Haven, Michigan in summer 2021. The first asexual propagation of 'SMNSBDOU' was carried out in summer 2021 by softwood cuttings at the same location in Grand Haven, Michigan. Through subsequent propagation, multiple additional generations have been reproduced, having shown that the unique features of this cultivar are stable and reproduced true to type.

SUMMARY OF THE INVENTION

The cultivar 'SMNSBDOU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNSBDOU'. These characteristics in combination distinguish 'SMNSBDOU' as a new and distinct *Spiraea* cultivar:

1. Bright orange spring flush.
2. Chartreuse-colored mature foliage that develops an orange tint, particularly at the tips of branches.

3. Vibrant orange and burgundy fall color.
4. Tidy, rounded habit.
5. Abundant, bright pink flowers.
6. Excellent container and landscape performance.
7. Foliage is healthy and resistant to disease (especially powdery mildew, *Microphaera penicillata*).

PARENTAL COMPARISONS

Parental comparisons are not available.

COMMERCIAL COMPARISON

'SMNSBDOU' can be compared to the commercial cultivar *Spiraea betulifolia* 'Tor Gold', unpatented. The two *Spiraea* are similar in most horticultural characteristics. The new cultivar, however, differs in the following:

1. Flower color of the new cultivar is bright pink, while the flower color of this comparator is white.
2. Foliage of the new cultivar is larger than the foliage of this comparator.
3. Leaf shape of the new cultivar is more elliptic, while the leaf shape of this comparator is more spherical (broadly elliptic).
4. Leaf serrations of the new cultivar are less defined than leaf serrations of this comparator.

BRIEF DESCRIPTION OF THE PHOTOGRAPHS

This new *Spiraea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Spiraea*.

DETAILED BOTANICAL DESCRIPTION

Figure 1:
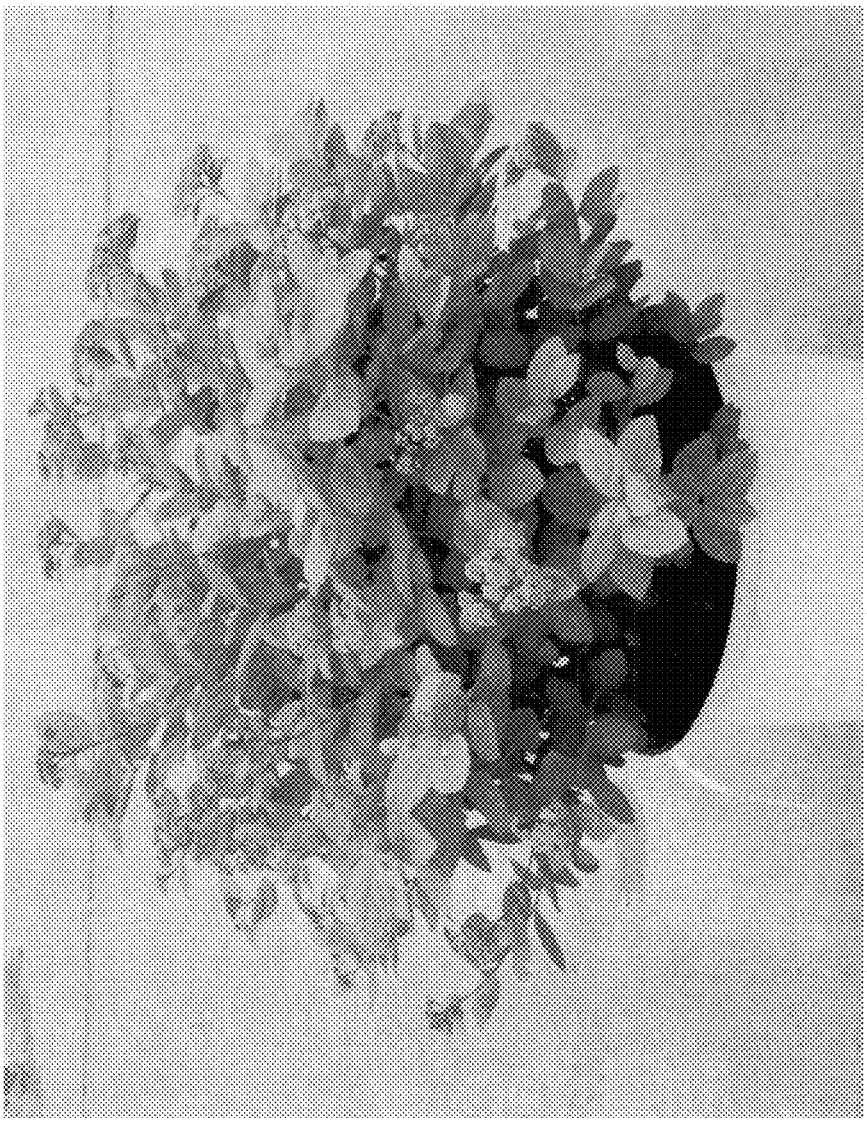
FIG. 1 is a color photograph showing a plant of 'SMNSBDOU' in Grand Haven, Michigan with flowers beginning to open. The plant is approximately 2.5 years old, growing in a 2 gallon pot.
Figure 2:
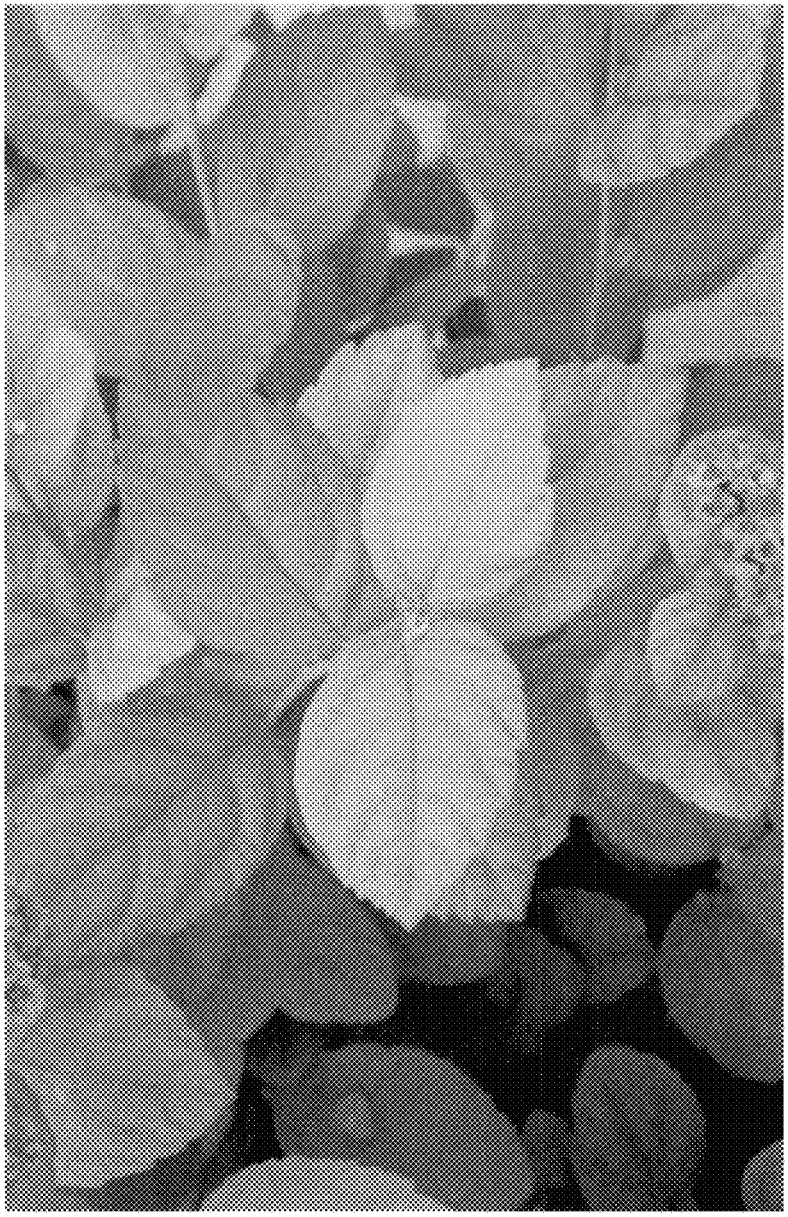
FIG. 2 is a close-up view of the foliage.
Figure 3:
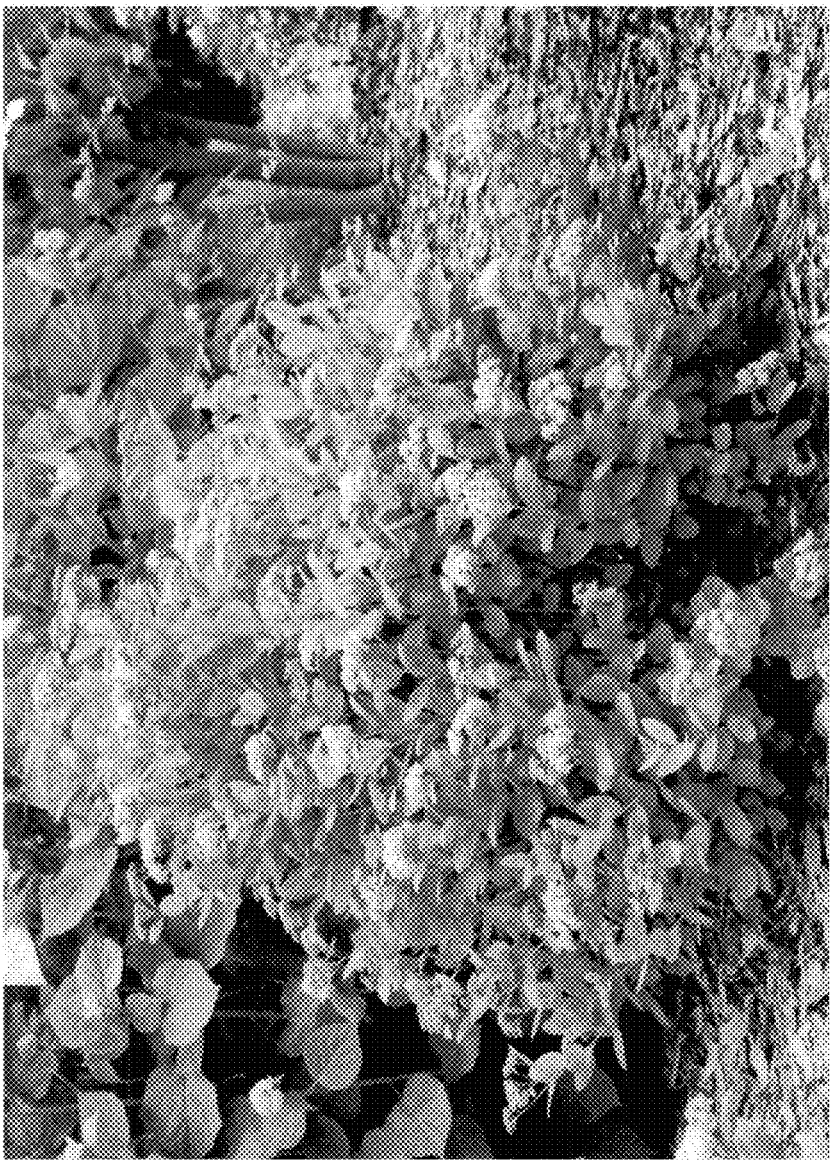
FIG. 3 is a color photograph of a 7-year-old plant growing outdoors in Grand Haven, Michigan.
Figure 4:
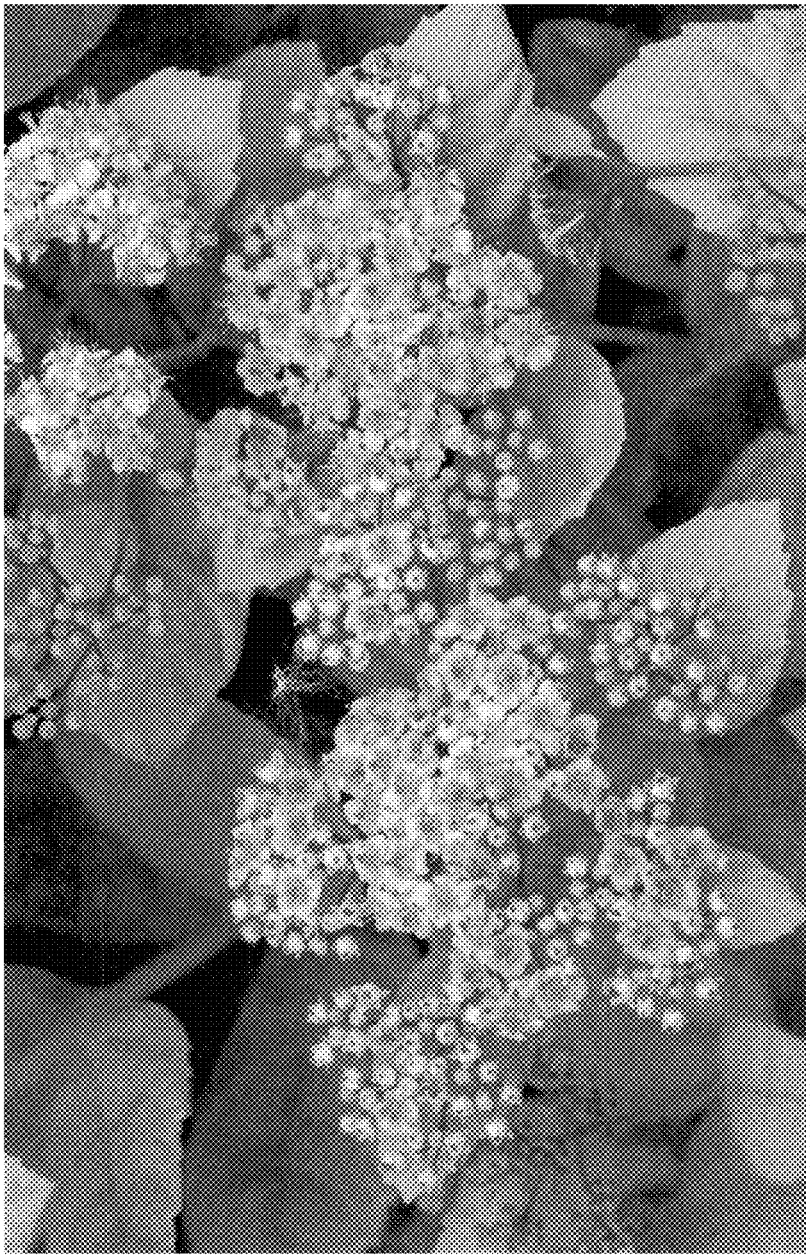
FIG. 4 shows inflorescences and mature foliage of 'SMNSBDOU' in Grand Haven, Michigan.
Figure 5:
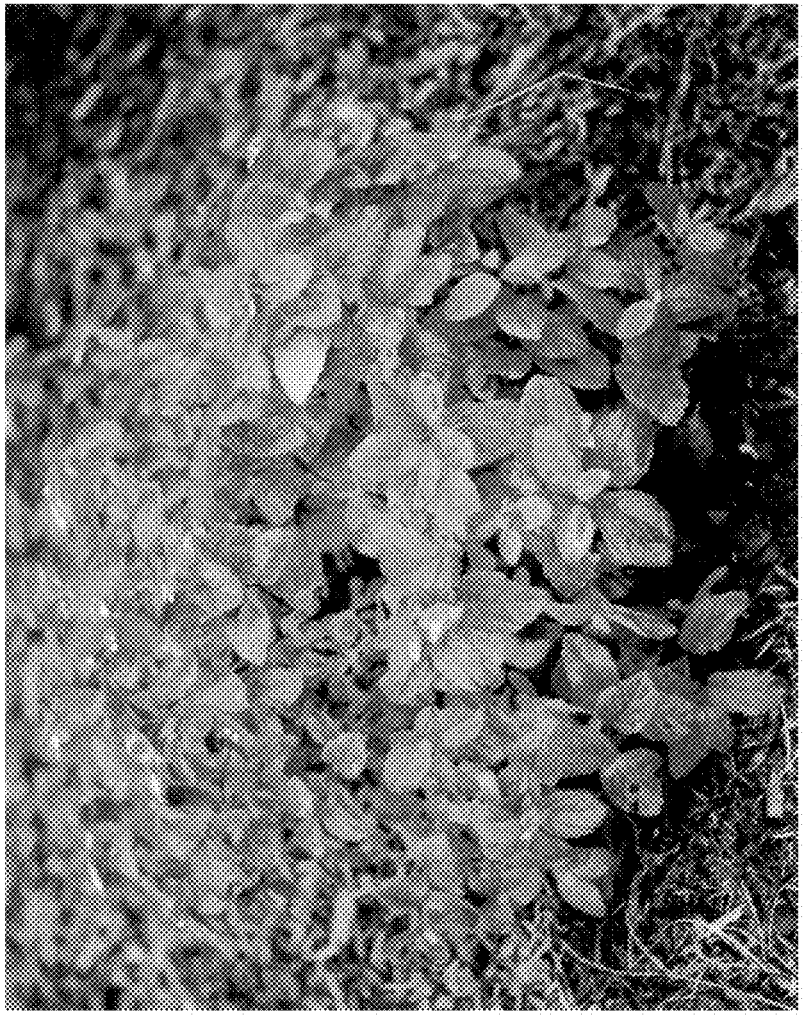
FIG. 5 is a color photograph of a 3-year-old plant growing outdoors in Grand Haven, Michigan with typical fall foliage.

In the following description, color references are made to The Royal Horticultural Society Colour Chart 2015, except where general terms of ordinary dictionary significance are used. The following observations and measurements describe 'SMNSBDOU' plants grown in a poly-greenhouse in Grand Haven, Michigan. The plants were 2 to 3 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Spiraea betulifolia* 'SMNSBDOU'.

PROPAGATION

Typical method: Softwood cuttings.
Root initiation: 15 days in summer at approximately 25° C.
Time to produce rooted cutting: About 60 days in summer at approximately 25° C.
Roots: Moderately dense, freely branching, fine, fibrous. Off-white to tan in color, not accurately measured with R.H.S. chart.

PLANT

Plant type: Perennial shrub.
Growth habit: Compact, rounded.
Shape: Globose.
Height: 45 cm.
Plant spread: 65 cm.
Pot size of plant described: 3 gallon.
Age of plant described: 2 to 3 years.
Stem:
- *Branching*.—Basal.
- *Pinching*.—Some required to encourage well-rounded habit.
- *Number of lateral branches*.—Around 50.
- *Shape*.—Rounded.
- *Color*.—Immature: RHS Yellow-Green 145A. Mature: RHS Greyed-Orange N167A.
- *Length*.—40 cm.
- *Width*.—3 mm.
- *Aspect*.—0° to 20° from vertical.
- *Strength*.—Medium.
- *Pubescence*.—None.
- *Internode Length*.—1.5 cm.

FOLIAGE

Leaf:
- *Arrangement*.—Alternate, single.
- *Shape*.—Ovoid to elliptic.
- *Length*.—3.5 cm.
- *Width*.—2.25 cm.
- *Apex*.—Broadly acute.
- *Base*.—Cuneate.
- *Margin*.—Crenate to serrate.
- *Texture of top surface*.—Glabrous.
- *Texture of bottom surface*.—Glabrous with raised venation.
- *Pubescence*.—None.
- *Color*.—Young Foliage, Upper Side: RHS Yellow-Green N144C with a Yellow-Green N144A tint. Young Foliage, Under Side: RHS Yellow-Green N144C with a Yellow-Green N144A tint. Mature Foliage, Upper Side: RHS Yellow-Green 144A. Occasionally flushed/blotched Orange-Red 34A and 34B. Mature Foliage, Under Side: RHS Yellow-Green 147B. Fall Foliage, Upper Side: RHS Greyed-Red 179A heavily flushed Red 46A and Orange-Red N34A. Fall Foliage, Under Side: RHS Greyed-Red 179A.

Venation:
- *Type*.—Pinnate.
- *Color*.—Mature, Upper Side: RHS Yellow-Green 144C. Mature, Under Side: RHS Yellow-Green 144C.

Petiole:
- *Length*.—2 mm.
- *Width*.—1 mm.
- *Color*.—Upper Side: RHS Yellow-Green 144C. Under Side: RHS Yellow-Green 144C.
- *Texture*.—Upper Side: Glabrous. Under Side: Glabrous.

INFLORESCENCE

Natural flowering season: Summer; May to June.
Flower arrangement: Terminal inflorescences.
Flowering habit: Terminal.
Inflorescence type: Compound corymb.
Height: 6 cm.
Diameter: 10 cm.
Quantity of flowers per inflorescence: About 100.
Quantity of inflorescences per lateral stem: About 20.
Quantity of flowers and buds per plant: About 4,000.
Fragrance: Mildly sweet and somewhat vegetal.
Flower:
- *Type or form*.—Rotate, single whorl.
- *Aspect*.—Upright.
- *Length*.—5 mm.
- *Diameter*.—5 mm.
- *Depth*.—3 mm.
- *Persistence*.—Persistent.
- *Longevity*.—About 2 weeks.

Bud:
- *Length*.—2 mm.
- *Diameter*.—2 mm.
- *Shape*.—Ovoid.
- *Color*.—RHS Red-Purple 64D.

Petals:
*Number.*—5.
*Arrangement.*—Stellate, single rotate.
*Shape.*—Globose
*Tip.*—Obtuse.
*Base.*—Obtuse.
*Margin.*—Entire.
*Length.*—2 mm.
*Width.*—2 mm.
*Texture.*—Upper side: Glabrous, silky. Under side: Glabrous, silky.
*Color.*—When Opening, Upper Side: RHS Red-Purple 64D. When Opening, Under Side: RHS Red-Purple 65D. Fully Opened, Upper Side: RHS Red-Purple 65A and 65B. Fully Opened, Under Side: RHS Red-Purple 65D. Fading, Upper Side: RHS Red-Purple 65D. Fading, Under Side: RHS Red-Purple 65D.

Sepals:
*Number.*—5.
*Arrangement.*—Whorl; inconspicuous.
*Shape.*—Triangular.
*Tip.*—Acute.
*Base.*—Fused.
*Margin.*—Entire.
*Length.*—1 mm.
*Width.*—1 mm.
*Texture.*—Upper side: Glabrous. Under side: Glabrous.
*Color.*—Mature, Upper Side: RHS Yellow-Green 144A. Mature, Under Side: RHS Yellow-Green 144A.

Calyx:
*Shape.*—Collar-like.
*Length.*—3 mm.
*Diameter.*—3 mm.

Peduncle:
*Terminal length.*—5 cm.
*Terminal diameter.*—3 mm.
*Angle.*—0° from vertical (in line with lateral branch).
*Strength.*—Moderate to high.
*Texture.*—Glabrous.
*Color.*—RHS Yellow-Green 144B.

Pedicel:
*Length.*—1 cm.
*Diameter.*—1 mm.
*Angle.*—45° from vertical.
*Strength.*—Moderate.
*Texture.*—Glabrous.
*Color.*—RHS Yellow-Green 144B.

REPRODUCTIVE ORGANS

Stamens:
*Number.*—About 10.
*Filament Length.*—2 mm.
*Filament color.*—RHS Red-Purple 65D.

Anthers:
*Shape.*—Globose.
*Length.*—1 mm.
*Color.*—RHS Red-Purple 65A.
*Pollen amount.*—Low.
*Pollen color.*—RHS Yellow 4D.

Pistil:
*Number.*—5.
*Length.*—2 mm.

Stigma:
*Shape.*—Rounded.
*Color.*—RHS Red-Purple 64C.
*Style length.*—2 mm.
*Style color.*—RHS Red-Purple 64C.
*Ovary color.*—RHS Yellow-Green 144A.

OTHER CHARACTERISTICS

Fruit and seed: Not observed.

Disease and insect resistance: Observed resistant to powdery mildew. Observed not to be susceptible to other typical foliar diseases. Neither resistance nor susceptibility to normal diseases and pests of *Spiraea* observed.

Temperature tolerance: Hardy in USDA Zones 3 to 9.

What is claimed is:

1. A new and distinct cultivar of *Spiraea* plant named 'SMNSBDOU' as herein illustrated and described.

* * * * *